United States Patent
Denton, III et al.

(10) Patent No.: US 9,420,779 B1
(45) Date of Patent: Aug. 23, 2016

(54) INSECT BAITS

(75) Inventors: Frank Russell Denton, III, Lawrenceville, GA (US); Ann Morgan Denton, Lawrenceville, GA (US); Jay James Hilbert Mullis, Danville, GA (US)

(73) Assignee: Green Dragon Pest Solutions, Inc., Macon, GA (US)

( * ) Notice: Subject to any disclaimer, the term of this patent is extended or adjusted under 35 U.S.C. 154(b) by 1352 days.

(21) Appl. No.: 12/590,520

(22) Filed: Nov. 10, 2009

Related U.S. Application Data

(60) Provisional application No. 61/198,941, filed on Nov. 12, 2008.

(51) Int. Cl.
*A01N 25/00* (2006.01)
*A01N 59/14* (2006.01)

(52) U.S. Cl.
CPC ............. *A01N 25/006* (2013.01); *A01N 59/14* (2013.01)

(58) Field of Classification Search
CPC .... A01N 25/002; A01N 25/006; A01N 59/14
See application file for complete search history.

(56) References Cited

U.S. PATENT DOCUMENTS

| | | | |
|---|---|---|---|
| 2,541,851 A | 2/1951 | Wright | |
| 3,167,440 A | 1/1965 | McVicker et al. | |
| 3,582,350 A * | 6/1971 | Werbin et al. | 426/578 |
| 3,767,422 A * | 10/1973 | Levitz | 426/331 |
| 5,182,879 A * | 2/1993 | Hopkins | 43/131 |
| 6,731,624 B1 | 3/2004 | Doane, Jr. et al. | |
| 2010/0210785 A1 | 8/2010 | Modell et al. | |

FOREIGN PATENT DOCUMENTS

| | | |
|---|---|---|
| JP | 401216907 A * | 8/1989 |
| WO | WO-2007/010095 A2 * | 1/2007 |

OTHER PUBLICATIONS

Andrea Widener, "What's That Stuff? Magic Sand and Kinetic Sand," C&EN, 93 (12): 41 (Mar. 23, 2015), at http://cen.acs.org/articles/93/i12/Magic-Sand-kinetic-Sand.html.
Andrew Turley, "The mystery of moon dough," (Dec. 2, 2010), (Chemistry World Blog, Roy. Soc. Chem. [UK]) at http://prospect.rso.org/blogs/cw/2010/12/02/the-mystery-of-moon-dough/.
Jackie, "Easy 2 ingredient cloud dough—ready in 5 minutes!," (Happy Hooligans, undated but no later than May 22, 2012) at http://happyhooligans.ca/cloud-dough/.
Rachelle Doorley, "Cloud dough recipe," (Tinkerlab®; undated but no later than Nov. 3, 2011), at http://tinkerlab.com/cloud-dough-exploration/.
Anna Ranson, "Snow dough recipe for winter sensory play," (The Imagination Tree: Nov. 27, 2012), at http://theimaginationtree.com/2012/11/snow-dough-recipe-for-winter-sensory.htm.
Anonymous, "Play-Doh FAQ & Tips," (Hasbro; undated; accessed May 20, 2015); at http://www.hasbro.com/playdoh/en_us/discover/faq.cfm.
Anonymous, "How to make moon sand," (WikiHow; undated; accessed May 20, 2015), posted at http://www.wikihow.com/Make-Moon-Sand.

* cited by examiner

*Primary Examiner* — Ali Soroush
(74) *Attorney, Agent, or Firm* — Denton Intellectual Property Law Firm, LLC; F. Russell Denton

(57) ABSTRACT

The invention provides an improved insect bait composition comprising a boric compound, a non-sugar low molecular weight compound having a plurality of hydroxyl groups, and a foodstuff comprising a substantial amount of a soluble or semi-soluble high molecular weight polysaccharide, wherein the high molecular weight polysaccharide is in a gelled form, the composition is a sustainably soft dough, and the foodstuff contains no more than 20 weight percent of a fat or oil. The composition is suitable for extrusion, is attractive and highly toxic to insects, and has excellent resistance to hardening and spoilage during its shelf life and after pesticidal application.

20 Claims, No Drawings

INSECT BAITS

RELATED APPLICATION

This application claims priority to U.S. Provisional Patent Application No. 61/198,941, filed Nov. 12, 2008, and having the same title.

FIELD OF THE INVENTION

This invention pertains to improvements in the formulation and use of baits for the extermination of cockroaches, ants, crickets, flies and other insects.

BACKGROUND

A number of insects infest human habitations, and methods to eradicate one type of insect are often effective against other unwanted insects. For instance roach and ant treatments may eradicate orthopterous species such as crickets, various types of flies, and other species. For parsimony's sake roaches and ants are discussed here as representative invasive species since they are among the most prevalent. Of the 4,000 species of roaches, 30 are associated with human habitations. The most invasive of these include the American cockroach (ca. 30 mm, 1.2 in.); German cockroach (ca. 15 mm, 0.5 in.), Asian cockroach (15 mm), and Oriental cockroach (25 mm, 1 in.). Most cockroach species adapt readily to a variety of environments, but they thrive in tropical and subtropical climates, and pest species especially prefer the warm conditions inside buildings. Ant infestations (order Hymenoptera) are also problematic; the worst invasive species include the pavement ant, yellow crazy ant, sugar ants, Pharaoh ant, carpenter ant, Argentine ant, odorous house ants, red imported fire ant and European fire ant.

The natural behaviors of these insects exacerbate infestations. Both roaches and ants leave chemical trails (by feces in the case of cockroaches) that other individuals of their same respective kind use to find food or water. Such trails also announce roach hiding places. Thus group behavior can be precipitated by a single individual's activity. Airborne pheromones likewise facilitate swarming and mating. Roaches and ants both reorganize their colonies quickly to adjust to changes in shelter conditions. However ants are diurnal, whereas for the most part roaches (with the exception of Asian cockroaches) are nocturnal and flee from light.

At a minimum, infestations are a nuisance, but they can also cause damage and illness. In a home, cockroaches and ants commonly feed on food, even pet food, as well as garbage, and they leave an offensive odor. See, e.g. R. J. Brenner, et al., *Infestations in Med.*, 4(8):349-355 (1987). Roaches are omnivorous, so they can damage personal property including wool, leather, paper, and the paste in book bindings. They are also a health hazard. Roach body surfaces passively transport human infectious diseases. C. Rivault, et al., *Epidemiol. Infect.*, 110(2):317-25 (April 1993); R. M. Elgderi et al., *Ann. Trop. Med. Parasitol.*, 100(1):55-62 (2006). Infestations also trigger allergic reactions in humans. H. S. Bernton and H. Brown. *J. Allergy*, 35:506-513 (1964); B. Kutrup, *Turk. J. Zool.*, 27:73-77 (2003). These allergens have been linked to asthma. B. Kang et al., *J. Allergy Clin. Immunol.*, 63(2):80-6 (1979).

Exterminating these pests can be daunting because their colonies are prolific and hardy, often with exponential growth. Cockroaches live for up to two years, depending on the species, and females commonly produce 300-400 eggs each, in some cases requiring only one impregnation for life or none at all. The nymphs hatch and reach adulthood in four months or less. Some species can go without air for 45 minutes or reduce their heart rate. American cockroaches can live three months without food and a month without water. And roaches can survive occasional freezing temperatures. Like many other insects, roaches are up to 15 times as radiation-resistant as humans partly because they are only specially genetically vulnerable during cell division at molting time. Consequently the easiest way to deal with infestations is to prevent them.

Physical preventative measures include storing all food in sealed containers, sealing garbage in tightly lidded cans, cleaning the kitchen frequently, and vacuuming regularly. Water taps and lines must be kept in good repair and insulated because drips even from condensation provide a water source for roach or ant colonies. And entry points, such as under baseboards, in between kitchen cabinets, and at pipes, doors and windows, must be blocked with steel wool or copper mesh and cement, putty or caulk. Unfortunately air-tight houses present their own problems, such as the retention of unwanted radium or mercury vapors that emanate from the ground and remain bound especially to particles in cigarette smoke that cling to walls. And if even one pregnant female roach enters the building such as by scurrying unnoticed through an open door, physical preventative measures may not exterminate the colony that forms as a result.

A severe alternative requires evacuating the premises for a few days while it is fogged by fumes from burning sulfur: the effects are said to last several years. However this not only displaces the human occupants, but also exposes walls and furnishings to the corrosive fumes, and requires precautions to avoid user asphyxiation, e.g., a gas mask.

Natural extermination methods are more attractive, but have had limited use. Cockroaches and ants have natural enemies including parasites and predators such as wasps and centipedes. Wasps are effective; those in the family Evaniidae attack roach egg cases, and those in the family Ampulicidae prey on adult and nymphal cockroaches (e.g., *Ampulex compressa*). The house centipede is probably the most effective control agent. Yet many homeowners do not want either type of predator in the house. Bunches of leaves of the Pandan plant (*Pandanus amaryllifolius* Roxb.) are said to be used as a roach repellant in Asian taxis. But their active compounds are volatile (thus less effective in dried leaves), and necessary concentrations may be hard to sustain in open air spaces.

In America the so-called Las Vegas trap has become popular, and also uses a natural approach. In this method coffee grounds or other food is placed with or without moisture into a slick glass open jar. The jar may be taped on the outside to facilitate climbing by the roaches, and greased inside with petroleum jelly to hinder escape up the sides, or the jar may simply be stood next to a wall. Such traps are useful for killing individual insects, sometimes a large number of them, however they do not tend to wipe out the entire colony nor do they kill live eggs that remain in the nest.

Partly because of these shortcomings of traps, professional exterminators prefer to use baits instead. The baits are toxic formulations that contain an attractant and are generally applied indoors. The baits are particularly effective because cockroaches and ants are cannibalistic, eating the corpses of downed individuals, cockroaches also eat their own feces, so the toxin is recycled and it kills additional individuals in each iteration of consumption by the colony. Baits are currently sold mostly in gel forms, under several brand names, including ADVANCE®, AVERT®, ADVION®, COMBAT®, DRAX®, INTICE®, SIEGE®, and MAXFORCE®, among others.

A typical bait gel's active ingredient is commonly hydramethylnon, fipronil, deltamethrin or pyrethrin. Baits that kill eggs can also reduce populations, but the results are slower. To convince end-users that the product works, even roach baits that employ the natural insect juvenile hormone—which is slow-acting—often include a "knock-down" additive poison to kill roaches on contact. Boric acid powder as well as borax are also toxic to cockroaches. Among the chemical alternatives, the boric compounds are the most natural, and are also relatively non-toxic to pets that might ingest them. The sharpness of fine boric acid crystals is thought to abrade cuticle and joints in the roach's exoskeleton, and boric acid also dehydrates. Boric acid is also used to exterminate flies such as fruit flies. www.bio.umass.edu/biology/kunkcl/cockroach_faq.html#U8.

For the more toxic compositions several manufacturers sequester the material in a bait station to prevent consumption by children or household pets, but this is not the only reason. Baits and sprayed insecticides have opposite mechanisms—a bait is a "trojan horse" whereas an insecticide kills on contact and repels—thus baits are often placed at a significant distance from any sprayed insecticide. Also, boric acid is washed away by water, thus direct use of the powder is limited to sites that are seldom wetted.

An illustrative roach bait is taught in U.S. Pat. No. 6,007,832, issued to Stapleton. The bait contains 15 to 35% boric acid, supplemented by one or more attractants and an additive selected from ascorbic acid, lipids, monosaccharides, gums, silica, and pectin. The attractant particularly disclosed was a dough of milk, onion, flour and sugar. The bait was disclosed to have a substantially paste or gelatinous consistency initially, adhering to surfaces, and within hours of application was said to dry as hard as plaster.

Master Roach Kill™, which was granted EPA pesticide registration no. 55540-20205 on a 1986 application by James Mullis, also contained milk, onion, flour, sugar and boric acid, but without the additives. It was marketed in the form of small balls; these also adhered to surfaces when fresh but hardened shortly after placement.

PCT Application No. WO 2007/010095 filed by Oy Finnpesticides Ltd. discloses a roach and ant bait composition of milk powder, onion, flour, sugar and boric acid, additionally containing water as well as 10-14 wt % potassium sorbate and 2-4 wt % each of alum, glycerine and citric acid.

Because of boric acid's effectiveness, natural source, environmental friendliness and low toxicity to humans and pets, it remains a preferred method to treat infestations of ants, roaches and other insects. However the presentation methods required for dry baits have fallen out of favor. For distribution the pesticide application industry prefers syringes, squeeze tubes, and caulk gun tubes; hard bait particles are not very compatible with this equipment. Moreover baits that remain soft and moist are more attractive to insects than are dry or hardened baits. Yet gels can often leave a sticky or unwanted residue after drying. Thus there is a continued need for improved formulations and processes that can provide the required physical and biological properties for baits.

BRIEF DESCRIPTION OF THE INVENTION

This invention provides insect bait formulations in a sustainably soft dough form that contains a boric compound, a non-sugar low molecular weight compound having a plurality of hydroxyl groups, and a foodstuff comprising a substantial amount of a soluble or semi-soluble high molecular weight polysaccharide, wherein the high molecular weight polysaccharide is in a gelled form, the composition is a sustainably soft dough, and the foodstuff contains no more than 20 weight percent of a fat or oil. The compositions are suitable for extrusion from applicator tubes. These formulations also remain moist, pliable, and unspoiled both during their shelf life and for an extended period after their application. The invention formulations are not only more attractive to insects than most existing baits on the market, but kill in significantly less time than commercial boric acid formulations from the prior art without the use of organic poisons that are highly toxic to humans and other mammals.

In one embodiment the invention provides an improved insect bait composition comprising a boric compound, a non-sugar low molecular weight compound having a plurality of hydroxyl groups, and a foodstuff comprising a substantial amount of a soluble or semi-soluble high molecular weight polysaccharide, wherein: (a) the high molecular weight polysaccharide is in a gelled form, (b) the composition is a sustainably soft dough, and (c) the composition contains no more than 20 weight percent of a fat or oil.

In a particular embodiment of the invention, the boric compound is selected from the group consisting of the acid, salt, and hydrate forms of the following: orthoboric acid, metaboric acid, paraboric acid, tetraboric acid, boron suboxide, boron oxide, boron sulfide, boron phosphate, and boron arsenate. In a further embodiment of the invention, the boric compound is present in the dough in the range of 20-80 weight percent.

In one embodiment of the invention, the non-sugar compound having a plurality of hydroxyl groups is a $C_{1-8}$ compound having at least two hydroxyl groups. In a more particular embodiment, the non-sugar compound having a plurality of hydroxyl groups is selected from the group consisting of glycerol, ethylene glycol, 1,2-propanediol, 1,3-propanediol, diethylene glycol, dipropylene glycol, triethanolamine, butanediols, catechol, pentaerythritol, and short oligomers of poly(vinylalcohol). In another embodiment of the invention, the non-sugar compound having a plurality of hydroxyl groups is present in the range of 10-50 weight percent of the composition.

In one embodiment the foodstuff in the improved insect bait is present in the range of 20-80 weight percent and is selected from the group consisting of grains, legumes, and tubers. In a further embodiment it comprises a comminuted grain selected from the group consisting of wheat, rye, barley, oats, millet, maize, rice, spelt, quinoa, and triticale. In another embodiment it comprises a comminuted legume selected from the group consisting of soybeans, navy beans, lima beans, peanuts and peas. In yet another embodiment the foodstuff comprises a comminuted tuber selected from the group consisting of potatoes, yams, beets, sweet potatoes, taro, and manioc.

In a particular embodiment of the invention the foodstuff in the improved insect bait comprises a fermented composition. In a different embodiment, the foodstuff further comprises a dairy product in the range of up to 30 weight percent. In yet another embodiment, the foodstuff comprises a substantial amount of a high molecular weight polysaccharide that is selected from the group consisting of amyloses, amylopectins, glycogen, food-grade celluloses and acidic polysaccharides. In a further embodiment, the foodstuff comprises a compound selected from the group consisting of hexoses, pentoses, disaccharides, and sugar alcohols. In a particular embodiment, the foodstuff further comprises plant material from a species in the genus *Allium*, such as edible parts of an onion, leek, garlic, shallot or other species of the genus *Allium*.

In one embodiment the invention provides a method of making an improved insect bait composition comprising: (a) providing ingredients comprising a boric compound, a non-sugar low molecular weight compound having a plurality of hydroxyl groups, and a foodstuff comprising a substantial amount of a soluble or semi-soluble high molecular weight polysaccharide; (b) combining the ingredients in any order, wherein the foodstuff having the high molecular weight polysaccharide is exposed to a liquid that has been heated immediately prior to combination at a temperature of at least 150° F., or wherein the foodstuff having the high molecular weight polysaccharide is combined with a liquid during which combination the foodstuff is heated at a temperature of at least 150° F.; and (c) mixing all ingredients until a sustainably soft dough is formed. In a further embodiment of the method the liquid comprises 10-50 weight percent of the sustainably soft dough, and the compound having a plurality of hydroxyl groups comprises at least 10-100 weight percent of the liquid.

In yet another embodiment the invention provides a kit for delivering an improved insect bait composition comprising (a) providing ingredients comprising a boric compound, a non-sugar low molecular weight compound having a plurality of hydroxyl groups, and a foodstuff comprising a substantial amount of a soluble or semi-soluble high molecular weight polysaccharide; (b) a bait delivery device whose smallest internal diameter for a nozzle, needle or extrusion pore is at least 1/16 inch inches for extrusion of the dough; (c) optionally a bait station or platform element to receive the extruded dough; and (d) optionally a handling element to facilitate manual pressing of the dough into crevices or onto surfaces. In a particular embodiment the kit's bait delivery device is selected from a syringe, a squeeze tube, a caulk gun tube, a pressurized can, and a pump device. In a further embodiment the optional bait station of the kit is selected from the group consisting of a non-adhesive floor placard, an adhesive wall placard, a perforated box, and a hollow tube having an inner diameter of about 1/8 to 1/4 inch.

DETAILED DESCRIPTION OF THE INVENTION

A roach bait must satisfy several requirements. In particular, although insects are omnivorous they have strong food preferences, thus they will not consume a bait when a more preferred alternative food is known to them. And even if they have no other alternative they do not consume their less preferred baits as quickly as their desired ones. Preferred foods for roaches and sugar ants are high in sugar or other carbohydrates such as starch, or have both; some other types of ants are attracted to high protein foods, and roaches are attracted to high protein foods such as milk. Roaches have complex scenting capacities, for instance they can associate aromatic scents of vanilla or peppermint with the potential for sweet food sources. And insects favor fresh produce; roaches are particularly fond of onion such as yellow onion, regardless of whether it is mixed with sweets or starches. Our experiments have found that when given a choice roaches disfavor foods that are high in fat or oil, and meat is not their most preferred food type. Roaches do, however, have a strong preference for fermented foods, such as beer.

The best baits are also moist and pliable. Insects consume traditional baits even after they have hardened, however they prefer baits that are still moist, possibly because such baits are softer or possibly because they represent a water source. Historically boric acid and other boric compounds have been used in bait form as a powder, or in a bait that hardens fairly rapidly after application. The inclusion of a fat or oil in a dough-like bait might make it more pliable, as disclosed by Stapleton in U.S. Pat. No. 6,007,832. However we have found that levels of fat or oil high enough to impart this property also make the bait less attractive to insects. Thus a sustainably doughy composition is needed with no more than minor dependence on fats or oils.

Particularly useful attractants are starchy or they contain starch-like polysaccharides, but traditional dough-type baits tend to harden. In our tests dough baits based on boric acid hardened like cement upon exposure to air. And we have observed that even in a sealed tube, within a few days an aqueous phase separates out spontaneously from an initially soft boric acid flour dough bait, leaving a tough, putty-like residue. The separated water there was not rejoined readily if at all by shaking the tube, and the tube had to be massaged vigorously to reduce the putty to a state that could be flowed, much like a thixotropic solid. Such manual rework of dough may be viable where the person applying it is willing to massage a squeeze tube and accept a liquid phase in the product from the nozzle. But this is not the most convenient solution, and massaging is also less viable for a syringe or caulk gun type of tube whose barrel has hard walls.

Baits should also resist spoilage, and this quality may be compromised in moist, doughy baits. Although a concentrated sample of a boric compound is a relatively hostile environment for microbial life, we have observed that mold can grow on doughy boric acid bait samples during storage. That is a particular problem for baits containing material such as onions, which tend to harbor mold spores due to their growth underground. The aroma from moldy roach bait is noxious: even if the insects did not shun it, the human end users would. In addition, we have found that the conditions under which roach baits are stored tends to result in rancidity when fatty or oily foodstuffs are present in the formulation, and this likewise creates an objectionable aroma.

Finally, even if a bait satisfies all the criteria enumerated above, it still may not be sufficient if it lacks fast-acting toxicity. Live roaches often continue to proliferate. And fast-acting baits ensure that the toxin is recycled more quickly and efficiently through the cannibalistic or coprophytic activity in the colonies.

Examples of prior developments in the art concerning soft baits, boric form, and attractants are shows below.

Pastes and Formed Gels

A number of food attractants have been formulated with toxicants and aqueous gel binders to provide toxic paste baits for cockroaches. U.S. Pat. No. 5,273,761 to Kim et al. teaches a method of killing roaches and ants by using an insecticidal composition consisting essentially of a mixture of boric acid, sugar, condensed milk, and an aqueous liquefier that is water or is bone or meat soup stock, where the mixture has a consistency ranging from a heavy cream to a paste.

Doi et al. [Chem. Abst. 107:129156n (1987)] controlled cockroaches with a paste containing boric acid, potato starch, corn starch, rice bran, molasses, water, and dye. Barson [Chem. Abst. 97:87017k (1982)] used a mixture of boric acid plus porridge oats and iodofenphos gel. Peeters [Chem. Abst. 84: 131508d (1976)] combined bakery wastes, boric acid, and water.

U.S. Pat. No. 5,968,540 issued to Brenner, et al. (United States as assignee) discloses a hydrodynamic bait for controlling a target insect comprising an attractant, high fructose corn syrup, glycerin as a humectant, and a pre-gelatinized gel former for starch.

U.S. Pat. No. 5,464,613 teaches the use of fat-based, substantially water-free, insecticidal compositions against insect pests such as cockroaches, ants, termites, flies, etc. As an example, the composition in the form of a paste can be applied into cracks and crevices for control of such pests and have the advantage of superior durability and prolonged attractiveness.

U.S. Pat. No. 4,988,510 issued to the United States discloses a packaged bait system for the control of insects, especially cockroaches and other orthopterous insects, comprising an insecticidal food bait composition housed in a bait block holder. The toxic bait comprised corn distiller's grain, a humectant, an insecticide and a gel former to yield a deformable hydrophilic gel matrix subsequent to hydration. Exemplary humectants were alcohol, sugar, and other polyhydroxy alcohols. In the preferred embodiment the insecticide was microencapsulated and in an example the bait was a block that had been dried at 300° C. for 48 hours and then further dried.

Boric Compounds

Boric acid and other boric compounds are known toxins for roaches, ants and fly baits. For instance, French patent 2,491, 296 (Lagache, 1982) discloses a 50:50 by weight composition of boric acid or one of its salts with sweetened condensed milk which was placed, without spreading, in a ship's hold to control cockroaches.

Japanese patent J5-4017-120 (Sakamoto) (Examined Japanese (JP) patent application publication B 47-23198 (1972)), discloses a cockroach bait of 1.5-10 weight percent boric acid, 10-50 weight percent starch and an extract of fish or animal bones prepared by boiling the bones in water for not over 2 hours.

The roach bait station sold under the trademark. "It Works" (Bridgeport, Conn.) is advertised as containing boric acid, an attractant, and a humectant.

Australian patent 22,579 (Fenwicke, 1935) teaches the use of boric acid as a "germicidal antiseptic" in combination with castor oil and turpentine as "cleaning agents" to be applied to sheep for killing maggots. Japanese patents J5-8052-205 (Nakamoto, 1981), J6-1030-506-A (Watkayama, 1984) and J6-1078-705-A (Amachir, 1984) teach the use of boric acid as the killing agent in various complex compositions for killing roaches (Nakamoto and Amachir) and white ants (Wakayama). All three Japanese patents involve a dry bait in a pellet, tablet or ball form. Also, Enkerlin, W. et al., "Use of a Mixture of Boric Acid, Borax, Hydrolyzed Protein, and Water to Control Anastrepha Fruit Flies," *Fruit Flies: Biology and Management*, ed. Alua, P. and Liedo, P., Springer-Verlag, NY, Inc., pp. 353-358 (1993) discusses the use of a toxic bait consisting of boric acid, hydrolyzed protein (PIB.7) and water to kill, for instance adult Anastrepha Ludens (Loew) and adult *Ceratitis capitaia* (Wied).

U.S. Pat. No. 4,205,066 (Hennant et al.) discloses insecticidal boric acid bait composition for anthropophilic flies.

WO/1999/013724 filed by the University of Florida teaches methods to control Tephritidae fruit flies, employing a borax toxicant being selected from the group consisting of borax, annhydrous borax, ammonium tetraborate, ammonium pentaborate, potassium pentaborate, potassium tetraborate, sodium metaborate, disodium tetraborate decahydrate, disodium tetraborate pentahydrate and disodium octaborate tetrahydrate U.S. Pat. No. 5,698,208 teaches use of borax toxicants to control tephritidae fruit flies.

Ken, A. J. et al.: Insect Pests Leaflets. Noll.-Fruit Flies, Gov't Printer, Dept. of Agriculture, N.S.W. Australia (1930) disclose the use of lures containing borax to trap Mediterranean and Queensland fruit flies. U.S. Pat. No. 4,440,746 (Maglio) is concerned with a granular pesticide composition which relies upon borax as a source of borate ions to effect gelation of polyvinyl alcohol.

U.S. Pat. No. 4,617,188 (Page) relates to natural insecticides employing borax and carob to control cockroaches.

J. K. Grace, et al., *J. Econ. Entomol,* 84(6):1753-1757 (1991) discusses the response of certain subterranean termites to borate dust and soil treatments.

W. Enkerlin, W. et al.: Use of a Mixture of Boric Acid, Borax, Hydrolyzed Protein, and Water to Control Anastrepha Fruit Flies, Fruit Flies: Biology and Management, ed. Aluja, P. and Liedo, P., Springer-Verlag, NY, Inc., pp. 353-358 (1993) suggest borate compounds may be used as insecticides against fruit flies and that a mixture of boric acid, borax, hydrolyzed protein and water may be used to control Anastrepha fruit flies.

Hogsette, J. A. et al.: J. Econ. Entomol., 85(4):1209-1212 (1992) compare toxicity of aqueous solutions of boric acid and polybor (disodium octaborate tetrahydrate) to house flies (Diptera: Muscidae).

Mullens, B. A. et al.: J. Econ. Entomol., 85(1):137-143 (1992) is concerned with the effects of disodium octaborate tetrahydrate (polybor) on the survival, behavior and egg viability of adult Muscoid flies (Diptera: Muscidae), i.e., house flies.

Lopez, F. D. et al.: J. Econ. Entomol., 61(1):316-317 (1968) disclose the use of pelletized lures formulated with borax and either PIB.7 (protein insect bait) or ENT-44, 014-X (enzyme hydrolyzed cottonseed protein) to trap and catch Mexican fruit flies.

Lopez, F. D. et al.: J. Econ. Entomol., 60(1):137-140 (1967) suggest that sodium borate inhibits decomposition of protein hydrolysates attractive to Mexican fruit flies.

The art teaches that boric acid must be kept dry because wet boric acid will not work for insecticidal purposes; see, e.g., Wellness Letter, University of Calif. at Berkeley, September 1991, page 7.

Attractants

Various food attractants have been formulated with toxicants and aqueous gel binders for insect baits. For example, Doi et al. [Chem. Abst. 107:129156n (1987)] controlled cockroaches with a paste containing boric acid, potato starch, corn starch, rice bran, molasses, water, and dye. Barson [Chem. Abst. 97:87017k (1982)] used a mixture of boric acid plus porridge oats and iodofenphos gel. Peeters [Chem. Abst. 84: 131508d (1976)] combined bakery wastes, boric acid, and water. Similarly, the proprietary roach bait station sold under the trademark, "It Works" (Bridgeport, Conn.) is advertised as containing boric acid, an attractant, and a humectant.

As noted above Doi et al. [Chem. Abst. 107:129156n (1987)] controlled cockroaches with a paste bait containing boric acid, potato starch, corn starch, rice bran, molasses, water, and dye. Barson [Chem. Abst. 97:87017k (1982)] used a mixture of boric acid plus porridge oats and iodofenphos gel. Peeters [Chem. Abst. 84: 131508d (1976)] combined bakery wastes, boric acid, and water.

The dried mash from a distillery was reported by Adler [J. Environ. Sci. Hlth. A20:839-844 (1985) to be specifically attractive for the brownbanded cockroch, *Supella longipalp* (F.). Brenner et al. [Ann. Entomol. Soc. Am. 81:581-592 (1988); J. Med. Entomol. 25:489-592 (1988); J. Econ. Entomol. 82:159-162 (1989)] reported that distiller's dried grains with solubles (DDGS, Agricultural Energy Corp., Franklin, Ky.) was attractive to 15 species of cockroaches including American cockroaches. Furthermore, the DDGS is unattractive to nontarget mammals, in contrast to other baits such as pieces of fruit, bread, and beer [Jackson et al., Am. J. Trop. Med. Hyg. 4:141-146 (1955), Ohio J. Scl. 61:220-226 (1961); Reierson et al., Pest Control 45: 40, 42-44 (1977); Fleet et al., Environ. Entomol. 7:807-814 (1978)] or dry cat food [Appel et al., Environ. Entomol. 14:669-673 (1985)] that are attractive to mammals as well as roaches.

Japanese document JA-72-23198-R (Sankyo Co. Ltd. 47-23198, [1972]) discloses a toxic roach bait comprising insecticidal compositions, e.g. dieldrin, BHC (Lindane), DDT, Sumithic, and boric acid mixed with more than 4 weight percent glycerol as a feed-behavior promoting agent in carriers such as cereal, fish meal, rice bran, starch paste, sugar, maltose, fatty acids, fatty acid esters and fatty alcohols. The exemplary baits were dried before use. The applicants observed that use of glycerine as a thickening agent below about 4 weight percent concentration does not stimulate feeding.

DEFINITIONS

Having described the problem and prior efforts by others to address it, we will now describe our invention in more detail. The following definitions are provided to clarify the meaning of terms as we use them.

The term "insect bait composition" as used herein refers to a composition containing material that is edibly attractive to an insect, in which the composition is toxic to the targeted insect population.

The term "sugar" as used herein has its usual and ordinary chemical meaning and includes hexoses, pentoses, disaccharides and amino sugars, but not sugar alcohols.

The term "sugar alcohol" as used herein has its usual and ordinary meaning.

The term "non-sugar compound" as used herein means a compound that is not a sugar. Particularly preferred non-sugar compounds for purposes of doughs made according to the invention are $C_{1-8}$ compounds having two or more hydroxyl groups. These compounds may optionally contain amine or thiol moieties instead of or in addition to hydroxyls. The non-sugar compound optionally has little or no toxicity to mammals.

The term "sweet compound" as used herein refers to a compound that is used for sweetening foodstuffs or found naturally in inherently sweet foodstuffs. Illustrative examples of sweet compounds include hexoses, pentoses, amino sugars, disaccharides, sugar alcohols, glycosides, sweet proteins, ethanol, and artificial sweeteners, but the invention is not so limited.

The term "sweet protein" as used herein refers to proteins that have sweet characteristics. Illustrative examples of a sweet protein are thaumatins, brazzein, monellin, pentadin, mabinlins, and neoculin, but the invention is not so limited.

The term "glycoside" as used herein has its usual and ordinary meaning in carbohydrate chemistry. Illustrative examples of glycosides include mogrosides and steviol glycosides, but the invention is not so limited.

The term "artificial sweetener" as used herein refers to a compound not found in nature that is used for sweetening foodstuffs. Illustrative examples of artificial sweeteners include sucralose, aspartame, and saccharin, but the invention is not so limited. The term "low molecular weight" as used herein refers to a compound having a molecular weight of less than about 200 daltons.

The term "high molecular weight" as used herein with respect to a polysaccharide refers to a molecule having 50 or more saccharide units.

The term "polysaccharide" as used herein refers to amyloses, amylopectins, glycogen, food-grade celluloses and acidic polysaccharides, including but not limited to starch, cellulose and modified celluloses, pectic substances, hemicelluloses, gums, poly(aminosaccharide)s, and other polysaccharides familiar to those in the art.

The term "gel" or "gelled form" as used herein with respect to the invention refers to a polysaccharide that has been heat treated in the presence of a liquid to stabilize it for long periods against crystallization and spontaneous separation of liquid from the polysaccharide during ordinary storage and pest treatment.

The terms "soluble" and "semi-soluble" as used herein with respect to a polysaccharide in the invention refers to the relative solubility of the polysaccharide in water.

The term "dough" as used herein with respect to the invention refers to a mechanically pliable insecticidal composition.

The term "sustainably soft dough" as used herein refers to a dough that does not become hard upon exposure to air or upon sitting in a sealed vessel for several weeks.

The term "liquid fraction" as used herein with respect to the mixing process refers collectively to liquids and optionally includes plant matter from any fresh *Allium* species that are mixed with those liquids and added to dry particulate matter to form dough.

When referring to the mass proportions of initial liquids relative to the final dough mass, the term liquid fraction as used herein refers collectively to the liquids alone as opposed to the *Allium* plant matter, and this is duly noted in the corresponding text.

The term "low evaporative component" as used herein with respect to the formulation of a liquid fraction refers to a liquid composition other than a dairy product that is combined with a dairy product or other liquid when preparing a dough made according to the invention, and that evaporates slowly if at all during use in an insect bait under ambient conditions of temperature, pressure and humidity. The low evaporative component is comprised in whole or in large part of one or more low molecular weight compounds that has a plurality of hydroxyl groups and or amine or thiol groups.

The terms "fat" and "oil" as used herein have their usual meanings in the art of food science.

The term "boric compound" as used herein with respect to the invention refers to a molecule wherein a boron atom is bonded to a plurality of oxygen or optionally sulfur or nitrogen atoms. In particular the term boric compound as used herein includes but is not limited to the acid, salt, and hydrate forms of the following: orthoboric acid, metaboric acid, paraboric acid, tetraboric acid, boron suboxide, boron oxide, boron sulfide, boron phosphate, and boron arsenate. The term boric compound as used herein refers both to single boric compounds and to combinations of boric compounds.

The term "salt" as used herein with respect to boric compounds has its usual and ordinary chemical meaning, and contemplates but is not limited to the ammonium, lithium, sodium, potassium, calcium, magnesium, iron, and manganese salts including mixed salts, and states intermediate between the salt-only form and the acid-only form. The term salt as used herein refers to single boric compounds and combinations of boric salts.

The term "acid" as used herein with respect to boric compounds has its usual and ordinary chemical meaning. The term acid as used herein refers both to single boric compounds and to combinations of boric salts.

The term "hydrates" as used herein with respect to boric compounds has its usual and ordinary chemical meaning. The term hydrate as used herein refers both to single boric hydrates and to combinations of boric hydrates.

The term "foodstuff" as used herein refers to components of the dough that are not boric compounds.

The term "comminuted" as used herein refers to providing size-reduced particles, as for flours and other powdered substances, e.g., from a milling process.

The term "flour" as used herein refers to an edible human foodstuff in powdered form, and includes both flours from a single food species and flours representing a combination of food species.

The term "grain" as used herein has its usual and ordinary meaning in the fields of botany and food science. Illustrative grains include but are not limited to wheat, rye, barley, oats, millet, maize, rice, spelt, quinoa and triticale.

The term "legume" as used herein has its usual and ordinary meaning in the fields of botany and food science. Illustrative legumes include but are not limited to soybeans, peas, navy beans and peanuts.

The term "tubers" as used herein has its usual and ordinary meaning in the fields of botany and food science. Illustrative tubers include but are not limited to potatoes, yams, beets, sweet potatoes, taro, and manioc such as tapioca.

The term "fermented" as used herein with respect to compositions has its usual and ordinary meaning in the field of food science. Illustrative fermented compositions include but are not limited to beer, wine, liquor, yogurt, cheese, and miso.

The term "dairy product" as used herein has its usual and ordinary meaning, but is not limited to dairy products from bovine sources. Illustrative dairy products include but are not limited to cow's milk, yogurt, cheese, cream, cottage cheese, cream cheese, goat's milk, and casein. The term dairy product as used herein refers to one or a combination of dairy products.

The term "genus *Allium*" as used herein refers to the plant genus as it is commonly recognized in botany and food science. Illustrative species of the genus *Allium* include but are not limited to onions, leeks, scallions, garlic, and shallots.

The terms "exposed to a liquid" and "combined with a liquid" as used herein with respect to the invention refers to the process of mixing solid with liquids to form a dough.

The term "kit" as used herein with respect to the invention refers to a kit for delivering an insect bait composition for insecticidal purposes.

The term "bait delivery device" as used herein with respect to the invention refers to a device for delivering a pliable dough for placement as an insect bait. Illustrative bait delivery devices include but are not limited to syringes, squeeze tubes, and caulk-gun-type tubes. The term "nozzle" as used herein with respect to a bait delivery device refers to the port for expressing the contents of the device.

The term "bait station" as used herein with respect to the invention refers to a housing for presenting insect bait to the target insect.

The term "platform element" as used herein with respect to the bait station refers to an open surface for presenting insect bait to the target insect.

The term "handling element" as used herein refers to a device such as trowel, scraper, plastic sheet, or other element for applying a dough of the invention to a crevice or other surface in an effective and penetrating way while keeping the user's hands clean.

The term "syringe" as used herein has its usual and ordinary meaning. That is, a syringe is a barrel having a nozzle at one end whereas the other end is open, whereby a plunger is propelled through the open end to force the barrel contents out of the nozzle.

The term "squeeze tube" as used herein refers to a tube that has a nozzle at one end and which is sealed at the other, such that pressure on the sides of the tube forces the contents of the barrel out of the nozzle. An illustrative squeeze tube is that commonly used for toothpaste.

The term "caulk gun tube" as used herein refers to a tube or barrel having a nozzle for extrusion on a first end and a movable wall on the second end that can be pushed toward the first end to apply the necessary pressure for extrusion. The term "caulk gun" as used herein refers to the application tool by which the second end of such a tube is mechanically leveraged for the extrusion, e.g., by ratcheting.

The term "extrusion pore" as used herein refers to the extrusion site for bait exiting a pressurized can or pump device.

The term "pressurized can" as used herein refers to a can in which the contents are under pressure, such as under gas pressure, whereby the internal pressure forces the contents out when a valve is opened.

The term "pump device" as used herein refers to a container wherein pumping action on one part of the device pressurizes the contents of the container such that they can be forced out when a valve is open.

The term "placard" as used herein refers to an open surface that can serve as a receiving element for insect bait, which can be slid on a surface if the placard is non-adhesive, or adhered e.g., to a wall if the placard is equipped with an adhesive surface.

The term "perforated box" as used herein refers to a container whose walls have at least one opening that is large enough to be entered by an insect that is targeted by bait placed inside the box.

The term "hollow tube" as used herein refers to a tube that may optionally be sealed on one or both ends, and the walls of which have at least one opening that is large enough to be entered by an insect that is targeted by bait placed inside the tube.

Preventing Separation of Liquid

We have found that although a superficially satisfactory dough may be prepared by merely mixing a starchy material with water, and although in theory the vitrifying effects of a boric compound might be expected to prevent recrystallization of starch in a well-mixed composition, such compositions nevertheless tend to harden spontaneously within days even in a sealed container. This is in contrast to the disclosure of U.S. Pat. No. 6,007,832, which teaches that a dough of boric acid powder, yellow onions, cane sugar, whole milk and flour after mere mixing can be packaged in tubes or sealed containers to prevent hardening until use.

We prevented this separation by mixing the liquid phase with the flour at an elevated temperature during manufacture. For wheat dough compositions, a temperature as low as 139° F. (ca. 59° C.) is known to provide partial solubilization, though ≥150° F. (ca. ≥64° C.) provides more complete solubilization. In alternative embodiments of the compositions, doughs with readily soluble polysaccharides based on crumbs, flour or starch of barley, potato or tapioca are heated to the same temperature ranges.

In still other embodiments in which moderately soluble starches are present, such as for a dough based on compositions from corn, rye, or peas, a temperature range of about 143-158° F. (ca. 62-70° C.) or higher is used.

In further embodiments in which even less hydrophobic starches are present, such as those involving rice, sago, sorghum or steam-treated potato, the temperature range is about 154-172° F. (68-78° C.) or higher.

Respective gelation conditions for alkyl celluloses, hemicelluloses, pentosans, glycogen, amylopectins, pectic substances, natural gums and other soluble or highly swellable high polysaccharides are known to persons of ordinary skill in the polysaccharide art, and may be used in still other embodiments of the present invention.

Particularly satisfactory results can also be achieved using temperatures in the range of 180-212° F. (ca. 82-100° C.), that is, in the range at the lower end of which water or milk simmers and at the upper end of which they boil. Enhanced pressure can likewise be used to facilitate solubilization. The presence of sugars and alcohols of low molecular weight is believed to slow the gelling process. However we have found that for small batches of the dough (e.g., one half to one kilogram) at atmospheric pressure, even when sugar is present the desired results can be achieved by adding a hot liquid. For instance simmering milk can be added to the dry ingredients with a few seconds of simultaneous rapid mixing. For large batches of dough it is more convenient to use alternatively or in addition a heated mixing vessel, such as a mixing bowl equipped with a steam jacket.

Low Molecular Weight Compounds Comprising a Plurality of Hydroxyl Groups

Boron is generally trivalent, but its vacant orbital can accept a lone pair of electrons such as from a hydroxyl oxygen to render the boron tetravalent. Also, the three hydroxyl groups of boric acid can be displaced readily and competitively by other hydroxyl groups, however the bidentate, chelation-like arrangement of oxygens in vicinal diols makes them particularly effective at displacing hydroxyl groups from other molecules at the boron center. Sugars and polysaccharides have many such neighboring hydroxyl features, thus it seemed possible that in prior art compositions boric acid combined with sugars and polysaccharides through an equilibration process to form cross links and generate a glass-like composition.

In order to reduce glass formation, we introduced low molecular weight, high boiling non-sugar compounds having a plurality of hydroxyl groups. Without being bound by theory, we believe condensation of these added hydroxyl groups with the boric centers may form energetically favored 5- to 8-membered rings in effective competition with similar ring formation by the sugars or starch in comparable chelation. Thus the hydroxyl groups in the added non-sugar compound are preferably bonded to carbons that are separated from one another by 0, 1, 2, or 3 other atoms in the molecule. The added non-sugar compound is preferably liquid at room temperature in the pure state, or if not liquid at room temperature preferably is formulated in combination with a second high-boiling compound that is both liquid at room temperature and substantially miscible with water and or the added non-sugar compound. By high boiling is meant, that a compound's boiling point in the pure state is substantially above 100° C. In one embodiment, that boiling point is ≥150° C.; in another embodiment it is ≥200° C. The high boiling point minimizes evaporation both during manufacture and after placement of the bait by the end user, i.e., this compound is a low evaporative component. The added non-sugar compounds also render the baits more resistant to spoilage and also appear to be well-tolerated by insect preferences.

In one embodiment suitable introduced low molecular weight, high boiling non-sugar compounds include glycerol, ethylene glycol, 1,2-propanediol, 1,3-propanediol, diethylene glycol, dipropylene glycol, triethanolamine, butanediols, butanetriols, and short oligomers of poly(vinylalcohol). Suitable mixed compounds include a glycol in combination with any of catechol or pentaerythritol or a sugar alcohol having four to six carbons. Compounds having amine or thiol groups may also be used and may in fact compete more effectively, however diols, triols and oligohydroxy compounds are preferred because their aroma is less objectionable.

Dough Compositions

The composition of choice for the foodstuff is determined by a combination of attractant effectiveness, texture requirement, and threshold lethality requirements.

Some of our tests have shown that onion baits in particular are preferred by roaches by as much as 39-69% over comparable non-onion baits. Yellow onions and Vidalia onions in particular are favorites with them, but white or red onions may be used instead. In other embodiments foodstuffs from other members of the genus *Allium* are contemplated, including species such as leeks, garlic, scallions, shallots, and so forth. The onions and other *Allium* foodstuffs may also be provided in dried form such as powder or flake for swelling in the liquid, though their odor is somewhat abated and using the dried product generally has a higher cost per ounce of material. It is also noted that preparations made according to the invention often have a diminished *Allium* aroma after formulation than doughs that are made without heat. In one embodiment the fresh food matter from a species of the *Allium* genus represents up to 20 weight percent of the total foodstuff. In another embodiment it represents 3-18 weight percent of the total foodstuff. In yet another embodiment it represents 6-16 weight percent of the total foodstuff. In a further embodiment it represents 9-14 weight percent of the total foodstuff. In another embodiment it represents 10-13 weight percent of the total foodstuff. In a particular embodiment food matter from a species of the *Allium* genus represents about 12 weight percent of the total foodstuff. Where dry matter from an *Allium* genus is used, each of the range boundaries for the percent of fresh *Allium* material in the total foodstuff may be divided by a factor between about 3 and about 10, e.g., where the dry matter from a species of the *Allium* genus represents up to 7 weight percent (i.e., up to ca. 20%×⅓) of the total foodstuff, and so forth.

Sweet baits are also popular with insects, and the sweetness of baits made according to the invention may be derived from a sugar, sugar alcohol, other natural alternatives, an artificial sweetener, or a combination thereof. The sugar alcohols tend to be less sweet by weight than sugars are. Illustrative sugars include but are not limited to sucrose, glucose, dextrose, fructose, and aminoglycans, as well as sweet glycosides. Non-exclusive examples of sweet glycosides include steviol glycosides and the mogrosides such as are found in the siraitia fruit. Illustrative sugar alcohols include but are not limited to glycol, glycerol, erythritol, arabitol, xylitol, ribitol, mannitol, sorbitol, isomalt, maltitol and lactitol. Illustrative natural alternatives include but are not limited to sweet proteins, for which illustrative non-exclusive examples are thaumatins, brazzein, monellin, pentadin, mabinlins, and neoculin. Illustrative artificial sweeteners include but are not limited to sucralose, aspartame and saccharin. All of these compounds in the pure form are solids at room temperature, except glycerol is liquid at room temperature; various glycols are similarly sweet and low-melting. In one embodiment a sweetener that in pure form is solid at room temperature represents up to 20 weight percent of the foodstuff. In another embodiment it represents 2-17 weight percent of the foodstuff. In yet another embodiment it represents 4-14 weight percent of the foodstuff. In a further embodiment it represents 6-11 weight percent of the foodstuff. In still another embodiment it represents 7-10 weight percent of the foodstuff. In a particular embodiment it represents 8-9 weight percent of the foodstuff.

Several types of flours are illustrated in the Examples, which vary in their intrinsic capacity for moisture absorption in the dough. E.g., in order for a rye flour dough to be soft it typically requires a higher weight percent of liquid than does a barley flour dough or wheat flour dough. And certain flours require the presence of a gummy substance such as pectin or tapioca in order to simulate a glutinous texture in the dough. In one embodiment the flour represents 5-35% of the foodstuff. In another embodiment the flour represents 7-30% of the foodstuff. In a third embodiment the flour represents 8-25% of the foodstuff. In yet another embodiment the flour represents 9-20% of the foodstuff. In a further embodiment the flour represents 10-15% of the foodstuff. In still another embodiment the flour represents 11-13% of the foodstuff. In a particular embodiment the flour represents about 12% of the foodstuff.

The amount of boric compound used can vary, and mixed boric compounds can be used, for instance a mixture of metaboric acid and boron phosphate, but in general ≥20 weight percent boric compound in the dough provides the fastest results. In one embodiment the boric compound represents 20-80 weight percent of the total mass of dough. In another embodiment it represents 25-70 weight percent of the total mass of dough. In a third embodiment it represents 30-60 weight percent of the total mass of dough. In yet another embodiment it represents 35-50% of the total mass of dough. In a further embodiment it represents 37-48% of the total mass of dough. In still another embodiment the boric compound represents 40-45% of the total mass of dough. In a particular embodiment the boric compound represents 42-43% of the total mass of dough.

The liquid fraction used can vary; fresh matter from *Allium* species is mostly water, so the amount of *Allium* matter used affects the amount of liquid that must be added during mixing. The liquid fraction may contain a dairy product or may optionally contain none, but will contain a low evaporative component. If any fresh matter from *Allium* species present is regarded as part of the dry mix merely for purposes of comparing mass proportions of added liquid, in one embodiment the low evaporative component represents 10-50 weight percent of the total mass of dough. The higher end of that range is more viable when the liquid is somewhat viscous as for diethylene glycol, and when fresh material from *Allium* species is absent. In a second embodiment the liquid component represents 15-40 weight percent of the total mass of dough. In a third embodiment it represents 17-30 weight percent of the total mass of dough. In yet another embodiment it represents 18-25 weight percent of the total mass of dough. In still another embodiment it represents 19-24 weight percent of the total mass of dough. In a further embodiment it represents 20-23 weight percent of the total mass of dough. In a particular embodiment it represents 21-22 weight percent of the total mass of dough.

Where a liquid fraction in dough is a combination of dairy product and low evaporative component, illustrative preparations according to the invention follow. Milk in its liquid and powdered forms is useful in the invention, as is casein. Milk that is low in fat is preferable, and fat free milk is particularly preferred because it avoids rancidity during shelf life. Doughs can be made with simply water instead of milk, however we have found that roaches prefer the dairy version. If any fresh matter from *Allium* species present is regarded as part of the dry mix merely for purposes of comparing mass proportions, in one embodiment the low evaporative component represents 10-95 weight percent of the total liquid fraction. The low end of that range is most viable when a large liquid fraction is used due for instance to the absence of fresh *Allium* plant matter and its corresponding native water content from a dough. In a further embodiment the low evaporative component represents 15-85 weight percent of the total liquid fraction. In a third embodiment it represents 25-75 weight percent of the total liquid fraction. In yet another embodiment it represents 35-65 weight percent of the total liquid fraction. In still another embodiment it represents 45-55 weight percent of the total liquid fraction. In a further embodiment it represents 48-52 weight percent of the total liquid fraction. In a particular embodiment the low evaporative component represents about 50 weight percent of the total liquid fraction.

Fatty and oily foods such as peanut butter and fried hamburger grease were substantially less preferred in our tests against roaches. This can be rationalized in part because oils applied to the surface of the exoskeleton can asphyxiate insects, which absorb their necessary oxygen through their abdomens. However protein (a source high in nitrogen) is known to be preferred over starch by some types of ants, even if it comes from fried meat. An additive such as bouillon powder may be included in the bait to give a meaty or savory aroma. Baits with a meaty savor may attract insect species that have a high protein requirement, as well as species that normally have a diet higher in vegetation but whose appetites have become more carnivorous due to presently inadequate amounts of protein in their diet. Where a small amount of non-fatty lubricant is desired in the bait it may be provided for instance by inclusion of lecithin, or by a substitute for fat such as an oligo(ethyleneoxide)glycol. Where fats are used, the addition of an antioxidant such as a tannin, other phenolic compound, carotene, other conjugated compound, or other antioxidant may delay rancidification caused by any exposure to air in the mixture. In one embodiment the foodstuff comprises up to 20% of a fat or oil. In another embodiment the bait comprises less than 15% fat or oil. In a third embodiment the foodstuff comprises less than 10% fat or oil. In yet another embodiment the foodstuff comprises less than 5% fat or oil. In yet another embodiment the foodstuff comprises less than 2% fat or oil. In yet another embodiment the foodstuff comprises essentially no fat or oil other than what is naturally present in the flour and optionally in the particles of an included *Allium* species.

Fermented attractants such as beer, wine or liquor may also be used, for instance in place of or in addition to an equal volume of milk. Any sweetener present should be selected such that combination with the fermented beverage does not result in bloating or bursting of the dough packaging by gas produced during its shelf life. Ethyl alcohol is recognized in nutrition and physiology as an third major energy source along with carbohydrates (to which proteins are converted by organisms) and fats; this rationalizes some of its appeal to insects. One concern with aromatic alcoholic beverages is that in a confined area with little ventilation their beverage scent may linger and be unacceptable to some consumers. However in our hands some experiments have found that roaches have a marked preference for an alcoholic beverages over another beverage such as milk. Also, in contrast to transient scent compounds, such as those of some vegetable or fruit produce that may oxidize or decompose and lose its distinctiveness within a period of days, the signature scents for beer and other alcoholic beverages are surprisingly stable and persistent over time.

We have found that the total liquid in the formulations of the instant invention discussed above may be substituted by an equal volume by a liquid comprising a fermented beverage such as beer or another alcoholic beverage. Just as for milk-containing doughs, doughs containing fermented products were likewise found to be stabilized by a low-evaporative liquid. The composition ranges shown above for milk-containing doughs and for low-evaporative non-sugar compounds having a plurality of hydroxyl groups, are similarly useful when an ethanol-containing beverage is used instead of the same volume of milk or other dairy product.

Dough Formulation

The order of combining ingredients in the formulation is not limited. For convenience' sake it was found to be particularly useful to combine the dry ingredients, e.g., by mixing them together. The dry mixing may optionally be by sifting ingredients together but sifting is not necessary to achieve effective dry mixing. The "wet" ingredients including the *Allium* species, dairy product and low evaporative component may also be conveniently combined and heated to a desired temperature. Generally while the liquid mix is still hot the dry mix can be added to it or vice versa; with rapid stirring this produced useful doughs within seconds.

EXAMPLES

Illustrative preparations are described below; this is not an exclusive list. With the exception of the white all-purpose wheat flour, potato starch and tapioca starch, which were purchased, all of the flours were obtained as a fine powder by grinding the corresponding grain or seed in a K TEC BLENDTEC® stoneless kitchen mill on its fine setting. The flours were mixed by stirring with the boric compound and other dry ingredients. The boric acid, borax, glycerol, and combined ethylene glycol/diethylene glycol used had technical grade purity, i.e., up to about 99% purity. The sugar was ordinary table sugar. The onion used was freshly diced yellow onion; onion powder or flake was used with comparable results in examples not described here. The milk was fresh fat-free milk, and the milk was present in a 50:50 mixture with the glycerol or diol of the example which was heated to a simmer with the diced onion, then the mixture was combined with the mixed powders and stirred briskly for about 30 seconds. The recipe ranges listed here are relatively uniform in order to illustrate the effect of identity changes in the formulation, but the invention is not limited to these ranges or to the exact order of mixing. Each formed dough was sealed in an air-tight transparent plastic bag and allowed to stand at room temperature for at least several days for observation; in several cases the products were reexamined for shelf life effects, and some were reexamined after having been stored for six months or more in a sealed plastic bag or in a syringe.

Example 1

Flour, Boric Acid and Glycerol

Doughs of the invention were made according to proportions shown in Table 1 below, where the milk mix and other components were prepared as stated in the paragraph immediately above, and where the other process steps were performed as described in that paragraph.

TABLE 1

| Type of Flour | Flour | Milk Mix* | Sugar | Onion | Boric Acid | Texture |
|---|---|---|---|---|---|---|
| Wheat (white flour) | 159 g | 180 g | 58 g | 80 g | 358 g | Soft, compressible dough |
| Corn (fine ground corn meal) | 159 g | 270 g** | 58 g | 80 g | 358 g | Initially very soft, stiffened within 48 hours to a grainy firmer dough |
| Rye | 159 g | 240 g | 58 g | 80 g | 358 g | Initially soft dough stiffened somewhat as it cooled |
| Millet | 159 g | 180 g | 58 g | 80 g | 358 g | Soft dough, slightly grainy |
| Spelt | 159 g | 180 g | 58 g | 80 g | 358 g | Like a soft clay |
| Oat (75% oat flour, 25% milled oats) | 159 g | 180 g | 58 g | 80 g | 358 g | Texture of oatmeal cookie dough, crumbly |
| Barley | 159 g | 180 g | 58 g | 80 g | 358 g | Like a fatty cookie dough, somewhat firm |
| White Rice | 159 g | 180 g | 58 g | 80 g | 358 g | Soft, crumbly dough, texture of coarsely mashed potatoes |
| Tapioca | 159 g | 180 g | 58 g | 80 g | 358 g | Like mashed potatoes |

*Containing equal parts milk and glycerol, and heated with the dry ingredients for about 30 seconds.
**Heated with the dry ingredients for about 2 minutes The doughs were stable over time, i.e., they remained soft, mold-free, and there was little or no separation of liquid from them. The samples were observed for periods of up to several weeks in air-tight sealed transparent plastic bags without spoilage or hardening. The consistency of some, such as the doughs based on corn and rye, becomes somewhat firmer in the first 24 to 48 hours. In the case of corn this is attributed to a longer heating time that was applied due to its slow absorption of liquid.

Samples of the dough based on wheat flour were allowed to stand for several weeks in the open air, and were observed in hot direct sun as well as at room temperature. In these conditions initially there appeared to be some moderate firming of the dough, possibly due to evaporation of water, after which they remained stable. Even after two months they remained soft and pliable, with no evidence of spoilage, rancidity, or mold. By contrast, for comparable samples of dough for which gelling had not been conducted, even dough in sealed bags tended to be susceptible to visible mold growth within a few days. Such samples also tended to exude liquid and become hard, such that shaking a sealed tube of the ungelled composition several days after its filling produced a watery rattling sound.

It was found that the diced onion pieces in gelled doughs tended to clog narrow nozzles when the dough was expressed from a tube. Using onion powder instead of diced onion avoided the clogging. Because dry onion powder represents a concentrated form of the onion, a lower weight can be used. In onion varieties used for dehydration, the dry weight of fresh onion is known in the art to have a typical range of 10-24% of the fresh weight by mass, but can be as low as 4% (in large bulbs with a high dry content of fructans) or as high as 35% in (in small bulbs), however the absolute amount of dry weight content per (mature) fresh bulb tends to be relatively constant. See D. S. Smith and J. N. Cash, *Processing Vegetables: Science and Technology* (1997), p. 212.

Variations, for instance use of milk with a 2% fat content, produced largely the same results.

Example 2

Flour, Boric Acid and Combined Ethylene Glycol/Diethylene Glycol

Doughs of the invention were made according to proportions shown in Table 2 below, using the same process steps as for Example 1. The doughs were stable over time, and were observed for periods of up to two weeks. The consistency of some samples, such as the doughs based on corn and rye, became somewhat firmer in the first 24 to 48 hours after mixing. The corn dough was mixed at an elevated temperature for only about 30 seconds, like the others.

TABLE 2

| Type of Flour | Flour | Milk Mix* | Sugar | Onion | Boric Acid | Texture |
|---|---|---|---|---|---|---|
| Wheat (white flour) | 79 g | 50 g | 29 g | 40 g | 179 g | Soft, compressible dough |
| Corn (fine ground corn meal) | 79 g | 57 g | 29 g | 40 g | 179 g | Soft dough, slightly crumbly |
| Rye | 79 g | 57 g | 29 g | 40 g | 179 g | Soft dough, but moderately firm |
| Millet | 79 g | 50 g | 29 g | 40 g | 179 g | Soft mashed potato texture |
| Oat (100% oat flour) | 79 g | 57 g | 29 g | 40 g | 179 g | Grainy, soft dough, slightly crumbly |
| Barley | 79 g | 50 g | 29 g | 40 g | 179 g | Soft dough, slightly crumbly |
| White Rice | 79 g | 50 g | 29 g | 40 g | 179 g | Like coursely mashed potatoes |
| Tapioca | 79 g | 50 g | 29 g | 40 g | 179 g | Mashed potato texture, somewhat flaky |
| Potato starch | 79 g | 50 g | 29 g | 40 g | 179 g | Like grainy mashed potatoes |
| Soybean | 79 g | 50 g | 29 g | 40 g | 179 g | Grainy and crumbly, porous and relatively non-absorbent |
| Brown rice/potato/tapioca/xanthan** | 79.3 g | 42.6 g | 29 g | 40 g | 179 g | Soft dough, slightly crumbly |

*Containing equal parts milk and ethylene glycol/diethylene glycol from an antifreeze mix; heated with the dry ingredients for about 30 seconds.
**Wheat-like non-glutenous flour mix (6 parts brown rice flour, 2 parts potato starch, 1 part tapioca flour), in which 79 g of the mix was supplemented by about 0.3 g xanthan gum powder Example 3

Flour, Borax and Combined Ethylene Glycol/Diethylene Glycol

Doughs of the invention were made according to proportions shown in Table 3 below, where the milk mix contained equal parts milk and ethylene glycol/diethylene glycol from an antifreeze mix. The doughs were stable over time, and were observed for periods of up to several days. The corn dough was mixed with heating for only 30 seconds like the others.

TABLE 3

| Type of Flour | Flour | Milk Mix | Sugar | Onion | Borax | Texture |
|---|---|---|---|---|---|---|
| Wheat (white flour) | 79 g | 50 g | 29 g | 40 g | 179 g | Like firm mashed potatoes; less absorbent than the boric acid analog |
| Corn (fine ground corn meal) | 79 g | 57 g | 29 g | 40 g | 179 g | Soft dough, remained soft |
| Rye | 79 g | 57 g | 29 g | 40 g | 179 g | Intermediate between soft and firm, somewhat fibrous and crumbly |
| Oat (100% oat flour) | 79 g | 57 g | 29 g | 40 g | 179 g | Crumbly dough |
| Barley | 79 g | 50 g | 29 g | 40 g | 179 g | Soft, doughy, |

TABLE 3-continued

| Type of Flour | Flour | Milk Mix | Sugar | Onion | Borax | Texture |
|---|---|---|---|---|---|---|
| White Rice | 79 g | 50 g | 29 g | 40 g | 179 g | slightly fibrous Like mashed potatoes, somewhat crumbly |

Example 4

Flour, Boric Acid and Combined Ethylene Glycol/Diethylene Glycol

A dough of the invention was made according to proportions shown in Table 4 below. The dough appeared to be stable and had a pleasant, nuanced aroma. The dairy mixture was comprised of 1 part by weight ethylene glycol/diethylene glycol mixture and 2 parts by weight yogurt that had been recently prepared and cultured in-house. The volume of sucralose used was equivalent in volume and sweetness to 29 g table sugar, though the actual mass of sucralose was only about 12% that of the sugar. The sucralose was obtained as SPLENDA®, manufactured by McNeil-PPC, Inc. The garlic had been freshly chopped.

TABLE 4

| Type of Flour | Flour | Dairy Mix | Sucralose | Garlic | Boric Acid | Texture |
|---|---|---|---|---|---|---|
| Wheat (white flour) | 79 g | 50 g | 3.5 g | 2 g | 179 g | Soft uniform dough |

Example 5

Delivery

A wheat-based dough prepared as in Example 1 was loaded into caulk-gun type tubes and also into 30 g syringes. The dough was readily and smoothly extrudable from either the tubes or the syringes to obtain a bait with a stable consistency like that of a soft clay.

Example 6

Efficacy

A wheat-based dough prepared as in Example 1 was tested by an independent entomological laboratory for its effect on German brown roaches and American roaches. The sample colonies included both males and females, and included nymphs as well as mature adults. The assays employed 1 g bait samples, and included control studies with no toxin as well as parallel studies of four leading commercial baits from other companies. In the competitive commercial baits, one listed only boric acid as the toxin, and three listed boric acid and an organic insecticide as active ingredients.

The insects in these studies showed a preference for the baits of the invention to the same degree as or more than for the other baits. Only the baits that contained the organic toxins had a faster kill rate than the exemplary invention bait. The invention sample was also superior to the competitive boric-only bait and was completely lethal against the tested roach populations in 7 days or less.

Example 7

Beer-Based Doughs

A soft wheat-based dough was prepared as in Example 1, but using the same volume of beer mixture instead of the volume of milk mixture. The beer mixture contained in one instance a 50:50 mixture by volume of Pabst Blue-Ribbon® Beer and glycerol. The beer mixture contained in a second instance half Natural Light® Beer and half glycerol by volume.

The latter dough was tested against 25 German Brown roaches in a 10 gallon aquarium containing open containers for ca. 4 oz. of dog food kibble and for 4 oz. water, along with 1 gram of the beer-based wheat dough bait and 1 gram of milk-based wheat-based dough bait, each bait being on a separate piece of aluminum foil. The milk-based dough bait was prepared as in Example 1. The roaches showed a 2:1 preference for the beer-based bait as opposed to the milk-based bait, as measured by the change in weight of the bait. All roaches consuming the bait died within 7 days; normally with an ample provision of non-toxic food and water in the test the roaches would survive for one year or even two in such tests, and would survive without for a month with no food or water. Examination of the Pabst Blue-Ribbon® sample after storage for over five months confirmed that the dough remained soft and that its beery scent was still potent and unspoiled.

From the description and claims herein, the invention and many useful permutations, variations, and derivatives of it will be apparent to the person having ordinary skill in the art of insect baits, and are contemplated within the scope of the invention.

We claim:

1. An improved insect bait composition comprising a boric compound, a non-sugar low molecular weight compound having a plurality of hydroxyl groups, and a foodstuff comprising a substantial amount of a soluble or semi-soluble high molecular weight polysaccharide, wherein
   a) the high molecular weight polysaccharide is in a gelled form,
   b) the composition is a sustainably soft dough, and
   c) the foodstuff contains no more than 20 weight percent of a fat or oil.

2. The composition according to claim 1 wherein the boric compound is selected from the group consisting of the acid, salt, and hydrate forms of the following: orthoboric acid, metaboric acid, paraboric acid, tetraboric acid, boron suboxide, boron oxide, boron sulfide, boron phosphate, and boron arsenate.

3. The composition according to claim 1 wherein the boric compound is present in the range of 20-80 weight percent.

4. The composition according to claim 1 wherein the non-sugar compound having a plurality of hydroxyl groups is a $C_{1-8}$ compound having at least two hydroxyl groups, optionally containing one or more amine or thiol moieties instead of or in addition to the hydroxyl groups.

5. The composition according to claim 1 wherein the non-sugar compound having a plurality of hydroxyl groups is selected from the group consisting of glycerol, ethylene glycol, 1,2-propanediol, 1,3-propanediol, diethylene glycol, dipropylene glycol, triethanolamine, butanediols, catechol, pentaerythritol, and short oligomers of poly(vinylalcohol).

6. The composition according to claim 1 wherein the non-sugar compound having a plurality of hydroxyl groups is present in the range of 10-50 weight percent.

7. The composition according to claim 1 wherein the foodstuff is present in the range of 20-80 weight % and comprises matter selected from the group consisting of grains, legumes, and tubers.

8. The composition according to claim 1 wherein the foodstuff comprises a comminuted grain selected from the group consisting of wheat, rye, barley, oats, millet, maize, rice, spelt, quinoa, and triticale.

9. The composition according to claim 1 wherein the foodstuff comprises a comminuted legume selected from the group consisting of soybeans, navy beans, lima beans, peanuts, and peas.

10. The composition according to claim 1 wherein the foodstuff comprises a comminuted tuber selected from the group consisting of potatoes, yams, beets, sweet potatoes, taro, and manioc.

11. The composition according to claim 1 wherein the foodstuff comprises a fermented composition.

12. The composition according to claim 1 wherein the foodstuff further comprises a dairy product in the range of up to 30 weight percent.

13. The composition according to claim 1 wherein the foodstuff comprises a substantial amount of a high molecular weight polysaccharide that is selected from the group consisting of amyloses, amylopectins, glycogen, food-grade celluloses and acidic polysaccharides.

14. The composition according to claim 1 wherein the foodstuff further comprises a compound selected from the group consisting of hexoses, pentoses, amino sugars, disaccharides, and sugar alcohols.

15. The composition according to claim 1 wherein the foodstuff further comprises plant material from a species in the genus *Allium*.

16. A method of making an improved insect bait composition comprising:
   a) providing ingredients comprising a boric compound, a non-sugar low molecular weight compound having a plurality of hydroxyl groups, and a foodstuff comprising a substantial amount of a soluble or semi-soluble high molecular weight polysaccharide wherein the foodstuff contains no more than 20 weight percent of a fat or oil;
   b) combining the ingredients in any order, wherein
      i) the foodstuff having the high molecular weight polysaccharide is exposed to a liquid that has been heated immediately prior to combination at a temperature of at least 150° F., or wherein
      ii) the foodstuff having the high molecular weight polysaccharide is combined with a liquid during which combination the foodstuff is heated at a temperature of at least 150° F.; and
   c) mixing all ingredients until the high molecular weight polysaccharide is in a gelled form and the composition is a sustainably soft dough.

17. The method of claim 16 wherein a liquid fraction comprises 10-50 weight percent of the sustainably soft dough, and wherein the compound having a plurality of hydroxyl groups comprises 10-100 weight percent of the liquid fraction.

18. A kit for delivering an improved insect bait composition comprising:
   a) the improved composition, comprising: a boric compound, a non-sugar low molecular weight compound having a plurality of hydroxyl groups, and a foodstuff comprising a substantial amount of a soluble or semi-soluble high molecular weight polysaccharide; wherein:
      i) the high molecular weight polysaccharide is in a gelled form;
      ii) the composition is a sustainably soft dough; and iii) the foodstuff contains no more than 20 weight percent of a fat or oil; and
b) a bait delivery device having a nozzle, needle or extrusion pore whose smallest internal diameter is no less than 1/16 inch;
c) optionally a bait station or platform element to receive the extruded dough; and
d) optionally a handling element to facilitate manual pressing of the dough into crevices or onto surfaces.

19. The kit according to claim 18 wherein the bait delivery device is selected from a syringe, a squeeze tube, a caulk gun tube, a pressurized can, and a pump device.

20. The kit according to claim 18 wherein the optional bait station is selected from the group consisting of a non-adhesive floor placard, an adhesive wall placard, a perforated box, and a hollow tube having an inner diameter of about 1/8 to 1/4 inch.

* * * * *